United States Patent
Hernandez Fernandez

(10) Patent No.: US 12,319,789 B2
(45) Date of Patent: Jun. 3, 2025

(54) PROCESS OF EXTRACTION, QUANTIFICATION AND RECOVERY OF ADDITIVES IN POLYPROPYLENE WITH NATURAL BIODEGRADABLE SOLVENTS AND USE OF THE POLYPROPYLENE RESULTING FROM THE MULTIPLE EXTRACTIONS

(71) Applicant: ESENTTIA S.A, Bolivar (CO)

(72) Inventor: Joaquin Alejandro Hernandez Fernandez, Bolivar (CO)

(73) Assignee: ESENTTIA S.A., Bolivar (CO)

( * ) Notice: Subject to any disclaimer, the term of this patent is extended or adjusted under 35 U.S.C. 154(b) by 637 days.

(21) Appl. No.: 17/630,296

(22) PCT Filed: Jul. 24, 2020

(86) PCT No.: PCT/IB2020/056983
§ 371 (c)(1),
(2) Date: Jan. 26, 2022

(87) PCT Pub. No.: WO2021/019390
PCT Pub. Date: Feb. 4, 2021

(65) Prior Publication Data
US 2022/0267557 A1    Aug. 25, 2022

(30) Foreign Application Priority Data
Jul. 30, 2019   (CO) .................. NC2019/0008355

(51) Int. Cl.
| | |
|---|---|
| C08J 11/06 | (2006.01) |
| B01D 11/02 | (2006.01) |
| B09B 3/80 | (2022.01) |
| B29B 17/02 | (2006.01) |
| B29B 17/04 | (2006.01) |

(52) U.S. Cl.
CPC .......... *C08J 11/06* (2013.01); *B01D 11/0284* (2013.01); *B01D 11/0288* (2013.01); *B01D 11/0292* (2013.01); *B09B 3/80* (2022.01); *B29B 17/02* (2013.01); *B29B 17/0412* (2013.01); *C08J 2323/12* (2013.01)

(58) Field of Classification Search
USPC ............................................ 528/190; 521/47
See application file for complete search history.

(56) References Cited

U.S. PATENT DOCUMENTS

2003/0191202 A1   10/2003   Maurer et al.
2015/0021422 A1   1/2015    Hall et al.

FOREIGN PATENT DOCUMENTS

| CN | 106279753 A | 1/2017 |
|---|---|---|
| WO | 2008064012 A2 | 5/2008 |

OTHER PUBLICATIONS

Moller J et al. Comparison of extraction methods for sampling of low molecular compounds in polymers degraded during recycling. European Polymer Journal, Jan. 6, 2008, vol. 44, No. 6, pp. 1583-1593, ISSN 0014-3057 (Year: 2008).*
Marianne Blazsó, Recent trends in analytical and applied pyrolysis of polymers, Journal of Analytical and Applied Pyrolysis, vol. 39, Issue 1 , Jan. 1997, pp. 1-25 (Year: 1997).*
Carrott M J. et al. Identification and analysis of polymer additives using packed-column Supercritical fluid chromatography with APCI mass spectrometric detection. Analyst Nov. 30, 1997, vol. 123, No. 9, pp. 1827-1833. (Year: 1998).*
Li Bo, et al., "Determination of Polymer Additives-Antioxidants, Ultraviolet Stabilizers, Plasticizers and Photoinitiators in Plastic Food Package by Accelerated Solvent Extraction Coupled with High-Performance Liquid Chromatography", Journal of Chromatographic Science, Jul. 2015, vol. 53, No. 6, pp. 1026-1035.
Okamoto Daichi, et al., "Development of Supercritical Fluid Extraction Coupled to Comprehensive Two-dimensional Supercritical Fluid Chromatography (SFE-SFCxSFC)", Analytical Sciences, Nov. 2006, vol. 22, No. 11, pp. 1437-1440.
International Search Report and Written Opinion for Corresponding International Application No. PCT/IB2020/056983, dated Oct. 1, 2020 with English Translation (19 pages).

* cited by examiner

*Primary Examiner* — Terressa Boykin
(74) *Attorney, Agent, or Firm* — LUCAS & MERCANTI, LLP

(57) ABSTRACT

A process of extraction, quantification and recovery of additives in polypropylene with the stages of washing the plastic material (A), grinding the material (A) to a particle size from 10 to 500 microns, extraction where the material (A) is transferred to a column (1) and then such material successively passes through column (2), column (3) and column (4), respectively, for successive extractions with solvents (I), (II), (III) and (IV), packed column extraction, where the solvent with the additives obtained from each extraction in columns (1), (2), (3) and (4) passes through packed columns (1'), (2'), (3') and (4'), respectively, crystallization of the additives obtained after each extraction stage in packed columns (1'), (2'), (3') and (4') respectively; and quantification of the additives obtained and where the residual material without additives is subjected to pyrolysis.

12 Claims, 1 Drawing Sheet

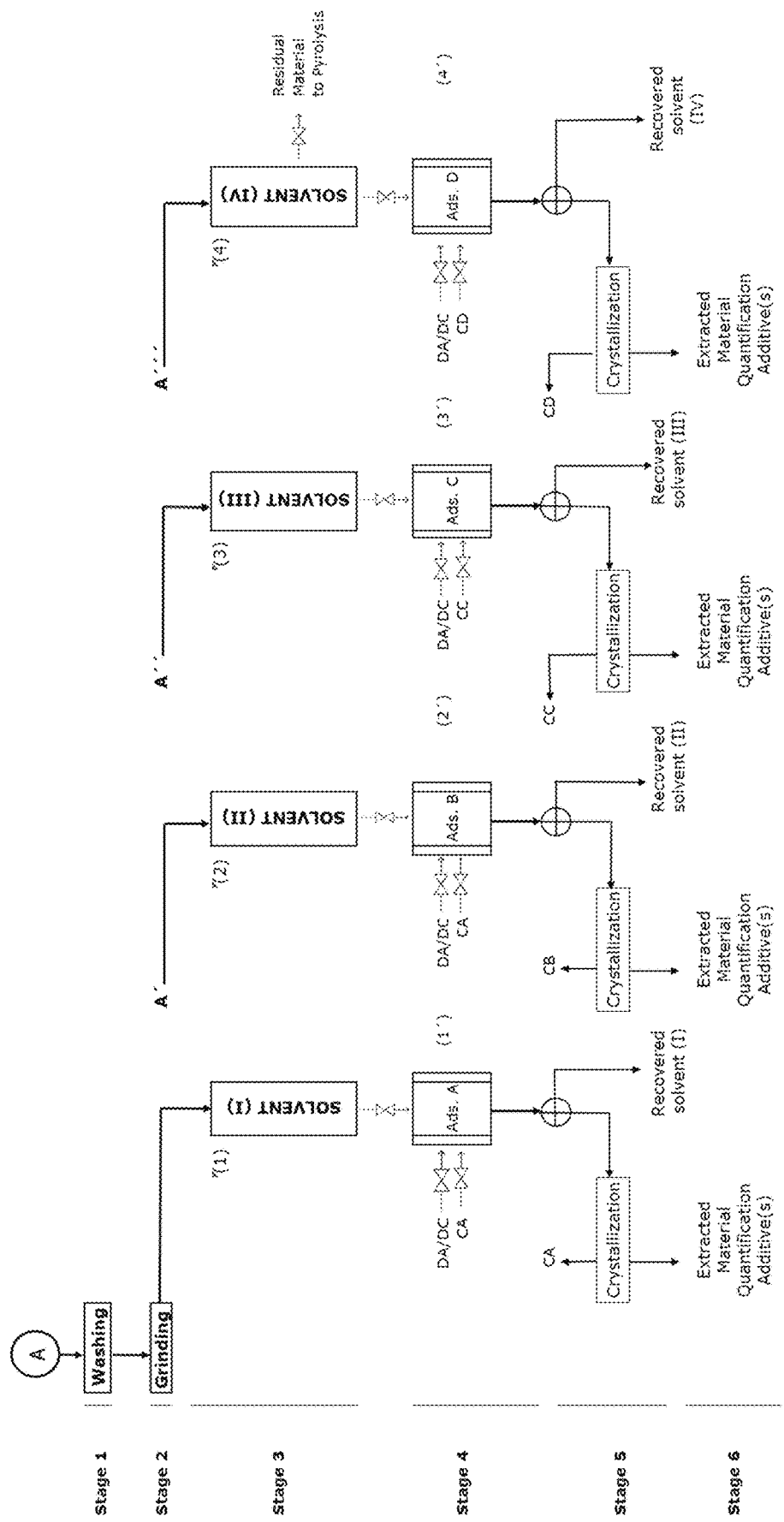

PROCESS OF EXTRACTION, QUANTIFICATION AND RECOVERY OF ADDITIVES IN POLYPROPYLENE WITH NATURAL BIODEGRADABLE SOLVENTS AND USE OF THE POLYPROPYLENE RESULTING FROM THE MULTIPLE EXTRACTIONS

CROSS REFERENCE TO RELATED APPLICATION

This Application is a 371 of PCT/IB2020/056983 filed on Jul. 24, 2020, which claims priority of Colombian Application No. NC2019/0008355 filed Jul. 30, 2019, each of which are incorporated herein by reference.

TECHNICAL FIELD

This invention falls within the framework of the field of the polymer industry and research, mainly within polypropylene additive recovery through natural biodegradable solvents. The invention also focuses on circular economy application insofar as the polypropylene resulting from the extraction may be reused or pyrolyzed with a lower energy consumption.

SUMMARY

This invention relates to a process for extraction, quantification and recovery of additives in polypropylene with natural biodegradable solvents based on cymene, myrcene (beta-myrcene), thymol, menthol, menthone, terpinol, limonene, pinene, borneol (2-canphanol), piperitone, citral, carvone, eugenol, citronellal, apiol, alpha bisabolol, chamazulene, tea tree, jasmine, German chamomile or matricaria, laurel, niaouli, sempervivum, linanol, eucalyptol (1,8-cineole), Lemon balm, caryophyllene, beta-caryophyllene, caryophyllene oxide, carene, phellandrene, pyrethrin camphor (2-canphanone), farnesol, vitamin A, beta-carotene, and other derivatives from monoterpenes, sesquiterpenes, diterpenes, phytosterols, phytostanols where the process comprises several stages of open loop recycling, closed loop recycling, Soxhlet, ultrasound, supercritical fluid and microwaves with solid phase extraction stages and purification through columns packed with materials allowing such extraction, quantification and recovery.

BRIEF DESCRIPTION OF THE FIGURES

FIG. 1 depicts a diagram of the process according to the invention.

BACKGROUND OF THE INVENTION

Polymeric plastic materials usually contain additives or chemicals needed to make such materials useful elements with desired physicochemical characteristics depending on the final application for which such material has been devised. In addition, the additives allow mixture stabilization and compatibilization during plastic processing stages.

Depending on said final application of the polymeric plastic materials, the additives may be, among others, flame retardant, stabilizing (antioxidant), foaming, plasticizers, ultraviolet light (UV) absorbent, antistatic and antibacterial additives. In the case of flame retardant additives, as the name suggests, they are applied to reduce material flammability and delay the spread of fire on the surface. In the case of stabilizers (antioxidants), there are substances that provide stability not only at the time of producing or transforming the material but also at the time of using the same in a given application in order to prevent undesirable characteristics such as, among others, discoloration, yellowing, loss of mechanical properties and rigidity.

On the other hand, foaming additives may be used to provide a foam-like isolating structure to the final product and provide the material with characteristics such as, among others, low density and volume. Plasticizers help increase the processability and flexibility of polymers by modifying their properties in glass transition state. The ultraviolet light absorbers provide greater stability and durability to polymers for outdoor applications by helping to extend their useful life. Antistatic and antibacterial additives, as their names imply, help prevent the formation of static charges in polymers and inhibit bacteria growth in polymers, respectively.

Given the importance of the repercussion of additives as agents that stabilize the structure of polymeric materials by making them practically impossible to degrade in the short term and the importance of recycling and reusing the elements comprising such materials without causing a greater damage to the environment, attempts have been made to recover the additives used in said polymeric materials.

In this regard, patent US2003/0191202 teaches a method for the separation of polymers and their additives from a polymer containing material, where the method is based on the principle of precipitation of the subject polymer and subsequent separation of the additives present in the solution. The separation of additives from the solution is effected in a further step. The method comprises the stages of material grinding and pre-cleaning, followed by a selective extraction and additional cleaning. A solvent is added after these stages, then the precipitation and drying is completed and a second solvent is added, which may differ from the first one and the additives present in the liquid phase are separated, mainly through distillation, where the solvents are tetrahydrofuran (THF), aliphatic ketones, alcohols and aromatic organic solvents.

The article "A rapid ultrasonic extraction technique to identify and quantify additives in poly(ethylene)" by Nadejzda et al. is also known, which teaches a procedure for analyzing aromatic antioxidants and UV stabilizers in polyethylene. The separation of the additives is carried out by ultrasound extraction with chloroform at 60° C. for separation of chimassorb 944 from a commercially available low density polyethylene film and separation of irganox 1010 and irgafos 168 from medium density polyethylene films. Quantification of the above is made through UV spectroscopy and HPLC with acetonitrile as mobile phase and at a 280 nm wave length. This investigation reports the effects of temperature, time and structure of additives as key factors affecting the efficiency of the extraction and reports that recovery was achieved after 15 minutes, 45 minutes and 60 minutes at 60° C. for Irgafos 168; Irganox 1010 and Chimassorb 944, respectively.

Another document related to the polypropylene recycling process is patent document CN106279753, which discloses a cross-linked polymer recovery process, which comprises the steps of: step 1) pretreating the waste cross-linked polypropylene: cleaning the surface by aspersion over and ultraviolet sterilization of the waste cross-linked polypropylene; step 2) depolymerization and recycling of the waste cross-linked polypropylene: breaking the cross-linked polypropylene waste treated in step 1), adding an extruder and depolymerizing a molecular chain of the cross-linked polypropylene under high temperature actions and alternating with shearing to carry out the recycling. The cross-linked polypropylene recycling process has the advantage of being more environmentally friendly and a more efficient process so that the depolymerized polypropylene is fluid at high temperature. The recycling process may be applied directly to the production of the product and solve pollution problems and the low efficiency of traditional treatment methods. In this case, the patent further teaches the recycling of all elements comprising the plastic material without making any differentiation or extraction of the same.

As it may be noted, even though the prior art teaches processes for using and recycling polymeric materials such as polypropylene and other polymers and an effort to try and separate the additives comprising the same, it is just as true that such processes/methods do not help to minimize environmental problems, on the contrary, they promote environmental pollution by employing biodegradable-resistant organic solvents during their stages.

Most processes that transform plastic waste or residues present in the environment for obtaining gas, propane, propylene, naphtha, ammonia, hydrogen, kerosene, etc. take the polypropylene (PP), grind it and introduce the same in a pyrolysis oven. Being the PP additivated and/or therm ically stabilized, then a higher amount of energy and oxygen is required in order to transform all such matter in the products and byproducts of interest. Additionally, the pyrolysis of this additivated residue generates greenhouse gases (SOX, NOX), toxic materials for health, such as, among others, dioxins and furans. The above is removed with this proposed invention given that the material will already be free of additives, whereby the pyrolysis of such material, already treated under the extraction and additive recovery process of this invention, is far more efficient and cleaner in comparison with the traditional ones, given that the energy consumption is lower since the material is no longer stabilized and the generation of greenhouse gases is also reduced. This is a technical advantage of the present invention given that most companies only pyrolyze with an open plume, thus emitting a significant volume of gases noxious for the environment.

In this regard, the present invention makes a signification contribution to the solution of the difficult extraction, quantification and recovery of additives comprising polymeric materials, either used or unused, which is achieved through a process of extraction, quantification and recovery of additives in polypropylene with natural biodegradable solvents such as limonene, pinene and other compounds or derivates from terpenes, hemiterpenes, monoterpenes, sesquiterpenes, diterpenes, triterpenes, polyterpenes and meroterpenes and mixtures thereof, where the extraction process comprises stages of open loop recycling, closed loop recycling, Soxhlet, ultrasound, supercritical fluid and microwaves with solid phase extraction stages and purification through columns packed with materials allowing such extraction, quantification and recovery.

The recovery of these additives in recycled material with a shorter life time prevent the migration of the same to water bodies or other environmental surroundings. Once such additives are recovered, the resin must be left with a high percentage of purity, that is, it is pure.

The high purity resin obtained after successive extractions may be reused or subject to a pyrolysis process. The pyrolysis of this material will have: lower energy consumption (given that oxidation is required of chains without thermal stabilizers), lower amount of combustion gases (NOX, SOX, DIOXINS, FURANS) and consequently, the pyrolysis process will be cleaner.

DETAILED DESCRIPTION OF THE INVENTION

The present invention is directed to a process, which may be carried out at a laboratory scale and easily implemented at an industrial scale, where the process comprises the following stages:

Stage 1: Washing;
Stage 2: Grinding;
Stage 3: Column extraction (1), (2), (3) and (4);
Stage 4: Packed column extraction (1'), (2'), (3') and (4'), respectively;
Stage 5: crystallization of additives obtained from each stage 4 extraction from packed columns (1'), (2'), (3') and (4'), respectively, and Stage 6: quantification and recovery of additives obtained.

In this regard the present invention covers a process of extraction, quantification and recovery of polypropylene additives and use of the latter, characterized in that the process comprises the following stages:

1. Washing the plastic material (A);
2. Grinding in a crushing or milling machine of material (A) up to a particle size from 10 to 500 microns;
3. Extraction where the material (A) of stage 2 is transferred to a column (1) and then, successively the material (A) passes through column (2), column (3) and column (4), respectively, being identified in each case as A'; A" and A''' for successive extractions with solvents (I), (II), (III) and (IV);
4. A subsequent stage of extraction in packed columns (1'), (2'), (3') and (4'), where the solvent with the additives obtained from each extraction from columns (1), (2), (3) and (4) passes through a packed column (1'), (2'), (3') and (4'), respectively;
5. A subsequent stage of crystallization of the additives obtained after each extraction stage in packed columns (1'), (2'), (3') and (4'), respectively and with the resulting recovery of the solvent; and
6. Quantification of the additives obtained and final disposal of the residual material "A" after the last extraction in column (4) through pyrolysis and where the additive free residue material is subjected to a subsequent pyrolysis process.

As depicted in FIG. 1, the plastic waste material (A), preferably from PP, PE, PVS and PS is subjected to stage one (1) washing with water at a temperature of 35° C. In stage two (2) grinding, the plastic waste material is subjected to a particle size reduction until obtaining particles with sizes from 50 to 100 microns. Subsequently in stage 3 extraction, this material is subjected to four extraction sub-stages, where the plastic waste material (A) remaining in the first column is subjected to a subsequent extraction in the following column until reaching the sub-stage in column (4).

In FIG. 1, each plastic waste material entering into the subsequent column after column (1) is identified with the letter A'; A" and A''. Columns (1), (2), (3) and (4) may be of any size and material, depending on the load amount of the material to be recycled, for example, the columns may be in glass material, stainless steel, aluminum or other resistant material for columns or towers used in industrial chemistry, where the columns may be conventional cylindric devices having a larger height than diameter. In the case of the extraction process at laboratory level, the columns may be, by way of example, but not limited to, borosilicate glass columns with a height of one meter and a nominal diameter of 12.7 cm (5 inches) and it may have inside one or several stainless-steel trays to hold the plastic waste (A), (A'); (A") and (A''') depending on the case and the column (1) to (4) where the material in the process is found.

The extraction product, that is, the solvent or mixture of solvents and dissolved components resulting from each column (1), (2), (3) and (4) passes respectively through a packed column (1'), (2'), (3') and (4'), where each packed column features a different packing comprised as follows:

The packed column (1')=contains from 85% to 95% of a modified styrene-divinilbenzene polymer (Strata X-33), preferably (90% of a modified styrene-divinilbenzene polymer (Strata X-33), from 7.5% to 2.5% of activated charcoal, preferably 5% of activated charcoal; and from 2.5% to 7.5% silanized glass wool), preferably 5%, The packed column (2')=contains from 80% to 90% of a modified styrene-divinilbenzene polymer (Strata X-33), preferably 85% of a modified styrene-divinilbenzene polymer (Strata X-33), from 7.5% to 15% of activated charcoal, preferably 10% of activated charcoal; and from 2.5 to 5% de salinized glass wool, preferably 5% of salinized glass wool, The packed column (3')=contains from 70% to 90% of a modified styrene-divinilbenzene polymer (Strata X-33), preferably 80% of a modified styrene-divinilbenzene polymer (Strata X-33), from 5% to 15% of activated charcoal, preferably 10% of activated charcoal; and from 5 to 15% de salinized glass wool, preferably 10% of salinized glass wool, and;

The packed column (4')=contains from 70% to 90% of a modified styrene-divinilbenzene polymer (Strata X-33), preferably 80% of a modified styrene-divinilbenzene polymer (Strata X-33), from 5% to 15% of activated charcoal, preferably 10% of activated charcoal; and from 5 to 15% de salinized glass wool, preferably 10% of salinized glass wool.

The element or component of a modified styrene-divinilbenzene polymer (Strata X-33) refers to a reversed phase functionalized polymeric sorbent which provides a strong retention of neutral, acidic or basic compounds under high and aggressive washing conditions, where this sorbent effects such retention through retention mechanisms, which are pi-pi bonds, hydrogen bonds, that is, dipole-dipole interaction and hydrophobic interactions. These packings allow separating the additives of interest in order to subsequently subject each one of the same to a crystallization sub-stage for obtaining crystalline additives, quantify the same and recover the solvent used in each one of the columns (1), (2), (3) and (4).

According to stage 1 of the process of extraction, quantification and recovery of additives of the invention, the plastic waste mixture (PP, PE and PVC), which may be either used or unused, termed (A) passes through a washing tank with water at a temperature from 20 to 50° C., more preferably from 30 to 40° C. and preferably 35° C. This tank features a mechanical agitation system for purposes of removing foreign matters from the material.

According to stage 2 of the process of extraction, quantification and recovery of additives of this invention, the material passes through a crushing or milling machine, which allows reducing the material particle size obtained from stage 1 washing in order to reach a particle size from 10 to 500 microns, more preferably from 20 to 200 microns and more preferably from 50 to 100 microns.

Once the material reaches the desired particle size, stage 3 column extraction starts, where extraction is made of each one of the additives of interest. To this end there are four columns (1), (2), (3) and (4) filled with different solvents, each column has a controlled heating system, ultrasound system or microwave and/or supercritical fluid. The following procedures are completed in this stage 3 extraction in columns (1), (2), (3) and (4) according to the present invention:

The recycled polymeric material (A) is transferred to column (1) and solid-liquid extraction is performed from 2 to 3 hours, using as solvent (I) 1-Methyl-4-(1-methylethenil)-cyclohexene (limonene). Column (1) is heated to a temperature from 40 to 70° C., more preferably 60° C. and energy is applied by ultrasound or radiation by microwaves. Then, the solvent enriched with the additives extracted in column (1) is subjected to stage 4 packed column extraction, specifically separation in the packed column (1"), which contains from 85% to 95% of a modified styrene-divinilbenzene polymer (Strata X-33), preferably 90% of a modified styrene-divinilbenzene polymer (Strata X-33), from 7.5% to 2.5% of activated charcoal, preferably 5% of activated charcoal; and from 7.5% to 2.5% of silanized glass wool), preferably 5%. After the above, recovery is made of the solvent and additives cis-13-Docosenamide (Erucamide), cis-9-octadecenamide (oleamide) and Glycerol monostearate- Glycerol palmitate (GMS) go on to stage 5 crystallization, which is performed according to the basic concepts of crystallization in order to subsequently go to stage 6 quantification of additives obtained.

After treatment in column 1 with solvent (I), the recycled polymeric material, now termed (A'), passes through column (2), where solid-liquid extraction is carried out from 2 to 3 hours, using as solvent (II) a mixture of cyclohexane: 1-Methyl-4-(1-methylethenil)-cyclohexene (limonene) in ratios ranging from 20:80 to 80:20.

Column (2) is preheated to a temperature from 40 to 70° C., more preferably at 60° C. and energy is applied by ultrasound or radiation by microwaves. Subsequently, the solvent enriched with the additives extracted from column (2) is subjected to separation in packed column (2'), which contains from 80% to 90% of a modified styrene-divinilbenzene polymer (Strata X-33), preferably 85% of a modified styrene-divinilbenzene polymer (Strata X-33), from 7.5% to 15% of activated charcoal, preferably 10% of activated charcoal; and from 2.5 to 5% of silanized glass wool, preferably 5% of silanized glass wool. After the above, recovery is made of the solvent and the additive octadecyl-3-(3,5-di-tert-butyl-4-hydroxyphenyl)-propionate go on to stage 5 crystallization, which is carried out according to the basic concepts of crystallization in order to subsequently go to a final stage 6 quantification of the additives obtained.

After treatment in column (2), the recycled polymeric material, now termed (A"), passes through column (3), where solid-liquid extraction is carried out from 2 to 3 hours, using as solvent (III) a mixture of Toluene: cyclohexane in ratios that vary from 20:80 to 80:20. Column (3) is heated at a temperature from 40 to 70° C., more preferably 60° C. and energy is applied by ultrasound or radiation by microwaves. Subsequently, the solvent enriched with the additives extracted in column (3) is subjected to separation in packed column (3"), which has from 70% to 90% of a modified styrene-divinilbenzene polymer (Strata X-33), preferably 80% of a modified styrene-divinilbenzene polymer (Strata X-33), from 5% to 15% of activated charcoal, preferably 10% of activated charcoal, and from 5% to 15% of silanized glass wool, preferably 10% of silanized glass wool. Subsequently, recuperation is made of the solvent and the separated additives: octadecyl-3-(3,5-di-tert-butyl-4-hydroxyphenyl)-propionate (Irganox 1076), Pentaerythritol tetrakis (3-(3,5-di-tert-butyl-4-hydroxyphenyl)-propionate) (Irganox 1010), 1,3,5-trimethyl-2,4,6-tris (3,5-di-tert-butyl-4-hydroxybenzyil) benzene (Etanox 330), Tris(2,4-di-tert.-butylphenil) phosphite (irgafox 168), Bis (2,4-dicumylphenyl) pentaerythritol diphosphite (doverohos), 1,3,5-tris(4-tert-butyl-3-hydroxy-2,6-dimethylbenzyl)-1,3,5-triazine-2,4,6-(1H,3H,5H)-trione (cyanox 1790) go on to stage 5 crystallization, which is carried out according to basic crystallization concepts in order to subsequently go on to the final stage 6 quantification of the additives obtained.

After treatment in column (3), the recycled polymeric material, now termed (A"), passes through column (4), where solid-liquid extraction is carried out from 2 to 3 hours, using as solvent (IV) a mixture of Toluene: 1-Methyl-4-(1-methylethenil)-cyclohexene (limonene) in ratios that vary from 20:80 to 80:20. Column (4) is heated at a temperature from 40 to 70° C., more preferably 60° C. and energy is applied by ultrasound or radiation by microwaves. Subsequently, the solvent enriched with the additives extracted in column (4) is subjected to separation in the packed column (4"), which has from 70% to 90% of a modified styrene-divinilbenzene polymer (Strata X-33), preferably 80% of a modified styrene-divinilbenzene polymer (Strata X-33), from 5% to 15% of activated charcoal, preferably 10% of activated charcoal, and from 5% to 15% of silanized glass wool, preferably 10% of silanized glass wool. Subsequently, recuperation is made of the solvent and the separated additives: Pentaerythritol tetrakis (3-(3,5-di-tert-butyl-4-hydroxyphenyl)-propionate) (Irganox 1010), 1,3,5-trimethyl-2,4,6-tris (3,5-di-tert-butyl-4-hydroxybenzyil) benzene (Etanox 330), Tris(2,4-di-tert.-butylphenil) phosphite (irgafox 168), Bis (2,4-dicumylphenyl) pentaerythritol diphosphite (doverohos), 1,3,5-tris(4-tert-butyl-3-hydroxy-2,6-dimethylbenzyl)-1,3,5-triazine-2,4,6-(1H,3H,5H)-trione (cyanox 1790) go on to stage 5 crystallization, which is carried out according to basic crystallization concepts in order to subsequently go to the final stage 6 quantification of the additives obtained.

In an embodiment of the invention, columns (1'), (2'), (3') and (4') which participate in stage 4 of the process according to the present invention are packed in the order mentioned above, that is, the lower part of the column holds the largest ratio component, then the activated charcoal and on the upper portion the silanized glass wool. In another embodiment of the invention, the order to the components inside the column has the reverse order of the prior embodiment, that is, the component with the smallest proportion is at the bottom of the column, then the activated charcoal component and on the upper portion the component with the largest proportion.

The stage 5 crystallization is carried out through conventional crystallization techniques, such as, by selecting an adequate solvent for crystallization, addition of a solvent, hot filtration of impurities and cooling of the saturated dissolution contained in an adequate container in an ice bath and/or crystal seeded of the compound that acts as a crystallization nucleus.

Example of Method Efficiency Evaluation 600 grams of a pure PP and known concentration of additives of interest are taken as reference. Once the material reaches the desired particle size, the column extraction stage starts, where extraction is made of each one of the additives of interest. The 600 grams of polymeric material ground are transferred to column (1) and the solid-liquid extraction is carried out from 2 to 3 hours, using as solvent (I) 1-Methyl-4-(1-methylethenil)-cyclohexene (limonene). Column (1) is heated at a temperature of 60° C. and energy is applied by ultrasound or radiation by microwave. Subsequently, the solvent enriched with additives extracted from column (1) is subjected to stage 4 packed column extraction, specifically to a packed column separation (1"). Subsequently, recuperation is made of the solvent and the separated additives: cis-13-Docosenamide (Erucamide), cis-9-octadecenamide (oleamide) and Glycerol monostearate- Glycerol palmitate (GMS) go on to stage 5 crystallization, which is carried out according to basic crystallization concepts in order to subsequently go to the final stage 6 quantification of additives obtained. In this stage, recuperation is made from 90% to 95% of the additives mentioned above.

After treatment in column 1 with the solvent (I), the recycled polymeric material, now termed (A'), passes through column (2), where solid-liquid extraction is carried out from 2 to 3 hours, using as solvent (II) a mixture of cyclohexane: 1-Methyl-4-(1-methylethenil)-cyclohexene (limonene) in ratios that vary from 20:80 to 80:20. Column (2) was preheated to a preferred temperature of 60° C. and energy is applied by ultrasound or radiation by microwaves. Subsequently, the solvent enriched with the additives extracted in column (2) is subjected to separation in the packed column (2'). Subsequently, recovery is made of the solvent and the additive octadecyl-3-(3,5-di-tert-butyl-4-hydroxyphenyl)-propionate (Irganox 1076) which goes on to stage 5 crystallization, which is carried out according to basic crystallization concepts in order to subsequently go on to the final stage 6 quantification of the additives obtained, where the additive recovery was 70%.

After treatment in column (2), the recycled polymeric material, now termed (A"), passes through column (3), where solid-liquid extraction is carried out from 2 to 3 hours, using as solvent (III) a mixture of Toluene: cyclohexane in ratios ranging from 20:80 to 80:20. Column (3) is heated to a temperature of 60° C. and energy is applied by ultrasound or radiation by microwaves. Subsequently, the solvent enriched with the additives extracted in column (3) is subjected to separation in packed column (3'). Subsequently, recuperation is made of the solvent and the separated additives: octadecyl-3-(3,5-di-tert-butyl-4-hydroxyphenyl)-propionate (Irganox 1076), Pentaerythritol tetrakis (3-(3,5-di-tert-butyl-4-hydroxyphenyl)-propionate) (Irganox 1010), 1,3,5-trimethyl-2,4,6-tris (3,5-di-tert-butyl-4-hydroxybenzyil) benzene (Etanox 330), Tris(2,4-di-tert.-butylphenil) phosphite (irgafox 168), Bis (2,4-dicumylphenyl) pentaerythritol diphosphite (doverohos), 1,3,5-tris(4-tert-butyl-3-hydroxy-2,6-dimethylbenzyl)-1,3,5-triazine-2,4,6-(1H, 3H,5H)-trione (cyanox 1790) go on to stage 5 crystallization, which is carried out according to basic crystallization concepts in order to subsequently go to the final stage 6 quantification of the additives obtained, where the following percentages were found: 20% of octadecyl-3-(3,5-di-tert-butyl-4-hydroxyphenyl)-propionate (Irganox 1076), 80% of Pentaerythritol tetrakis (3-(3,5-di-tert-butyl-4-hydroxyphenyl)-propionate) (Irganox 1010), 90% of 1,3,5-trimethyl-2,4,6-tris (3,5-di-tert-butyl-4-hydroxybenzyil) benzene (Etanox 330), 85% of tris(2,4-di-tert.-butylphenil) phosphite (irgafox 168), 77% of Bis (2,4-dicumylphenyl) pentaerythritol diphosphite (doverohos), 81% of 1,3,5-tris (4-tert-butyl-3-hydroxy-2,6-dimethylbenzyl)-1,3,5-triazine-2,4,6-(1H,3H,5H)-trione (cyanox 1790).

After treatment in column (3), the recycled polymeric material, now termed A", goes to column (4), where solid-liquid extraction is carried out from 2 to 3 hours, using as solvent (IV) a mixture of Toluene: 1-Methyl-4-(1-methylethenil)-cyclohexene (limonene) in ratios ranging from 20:80 to 80:20. Column (4) is heated at a temperature of 60° C. and energy is applied by ultrasound or radiation by microwaves. Subsequently, the solvent enriched with the additives extracted in column (4) is subjected to separation in the packed column (4'). Subsequently, recuperation is made of the solvent and the separated additives: Pentaerythritol tetrakis (3-(3,5-di-tert-butyl-4-hydroxyphenyl)-propionate) (Irganox 1010), 1,3,5-trimethyl-2,4,6-tris (3,5-di-tert-butyl-4-hydroxybenzyil) benzene (Etanox 330), Tris(2,4-di-tert.-butylphenil) phosphite (irgafox 168), Bis (2,4-dicumylphenyl) pentaerythritol diphosphite (doverohos), 1,3,5-tris(4-tert-butyl-3-hydroxy-2,6-dimethylbenzyl)-1,3,5-triazine-2,4,6-(1H,3H,5H)-trione (cyanox 1790) go on to stage 5 crystallization, which is carried out according to basic crystallization concepts in order to subsequently go to the final stage 6 quantification of obtained additives, where said additives were found in the following percentages: 10% of Pentaerythritol tetrakis (3-(3,5-di-tert-butyl-4-hydroxyphenyl)-propionate) (Irganox 1010), 5% of 1,3,5-trimethyl-2,4, 6-tris (3,5-di-tert-butyl-4-hydroxybenzyil) benzene (Etanox 330), 5% of Tris(2,4-di-tert.-butylphenil) phosphite (irgafox 168), 10% of Bis (2,4-dicumylphenyl) pentaerythritol diphosphite (doverohos), 5% of 1,3,5-tris(4-tert-butyl-3-hydroxy-2,6-dimethylbenzyl)-1,3,5-triazine-2,4,6-(1H,3H, 5H)-trione (cyanox 1790).

Stage 5 crystallization is carried out through conventional crystallization techniques, such as, by selecting the adequate solvent for crystallization, adding the solvent, hot filtering of impurities and cooling down of the saturated dissolution contained in an adequate container in an ice bath and/or crystal seeded of the compound acting as crystallization nucleus.

The invention claimed is:

1. A process of extraction, quantification and recovery of additives in polypropylene comprising the following stages:
    stage 1) washing a plastic material (A);
    stage 2) grinding the plastic material (A) to a particle size from 10 to 500 microns;
    stage 3) carrying out an extraction process where the plastic material (A) of stage 2) is transferred to a first column and thereafter the plastic material (A) passes through a second column, a third column and a fourth column respectively for successive extractions with a first solvent, a second solvent, a third solvent and a fourth solvent, respectively, to obtain a first, second, third and fourth solvent with additives;
    stage 4) carrying out packed column extraction, wherein the first, second, third and fourth solvent with the additives obtained from each extraction in the first, second, third and fourth columns from stage 3) passes through a first packed column a second packed column, a third packed column and a fourth packed column respectively to obtain a first additive, a second additive, a third additive and fourth additive;
    stage 5) crystallizing the additives obtained from each extraction stage in the first, second, third and fourth packed columns respectively from stage 4); and
    stage 6) quantifying the crystallized additives obtained from stage 5);
    wherein a residue material without additives is subjected to a subsequent pyrolysis process,
    wherein in stage 4), the first, second, third and fourth packed columns each comprises a different packing, and wherein
    the first packed column contains from 85% to 95% of a modified styrene-divinylbenzene polymer (Strata X-33), from 7.5% to 2.5% of activated charcoal and from 2.5% to 7.5% of silanized glass wool;
    the second packed column contains from 80% to 90% of a modified styrene-divinylbenzene polymer (Strata X-33), from 7.5% to 15% of activated charcoal and from 2.5% to 5% of silanized glass wool;
    the third packed column contains from 70% to 90% of a modified styrene-divinylbenzene polymer (Strata X-33), from 5% to 15% of activated charcoal and from 5% to 15% of silanized glass wool; and
    the fourth packed column contains from 70% to 90% of a modified styrene-divinylbenzene polymer (Strata X-33), from 5% to 15% of activated charcoal and from 5% to 15% of silanized glass wool.

2. The process of extraction, quantification and recovery of additives in polypropylene according to claim 1, wherein stage 1) is performed at a temperature from 20 to 50° C.

3. The process of extraction, quantification and recovery of additives in polypropylene according to claim 1, wherein in stage 2), the grinding is carried out in a crushing or milling machine and the particle size is from 20 to 200 microns.

4. The process of extraction, quantification and recovery of additives in polypropylene according to claim 1, wherein in stage 3), each column has a controlled heating system, ultrasound, microwave or supercritical fluid system.

5. The process of extraction, quantification and recovery of additives in polypropylene according to claim 1, wherein in stage 3), a solid-liquid extraction is performed in the first column from 2 to 3 hours with the first solvent, wherein the first solvent is 1-Methyl-4-(1-methylethenil)-cyclohexene (limonene) and the first column is heated to a temperature from 40 to 70° C. and energy is applied by ultrasound or radiation by microwaves.

6. The process of extraction, quantification and recovery of additives in polypropylene according to claim 1, wherein in stage 3), the second column contains the second solvent, wherein the second solvent is a mixture of cyclohexane: 1-Methyl-4-(1-methylethenil)-cyclohexene (limonene) in ratios ranging from 20:80 to 80:20 and the second column is heated to a temperature from 40 to 70° C. and energy is applied by ultrasound or radiation by microwaves.

7. The process of extraction, quantification and recovery of additives in polypropylene according to claim 1, wherein in stage 3), the third column contains the third solvent, wherein the third solvent is a mixture of toluene: cyclohexane in ratios ranging from 20:80 to 80:20 and the third column is heated to a temperature from 40 to 70° C. and energy is applied by ultrasound or radiation by microwaves.

8. The process of extraction, quantification and recovery of additives in polypropylene according to claim 1, wherein in stage 3), a solid-liquid extraction is performed in the fourth column from 2 to 3 hours with the fourth solvent, wherein the fourth solvent is a mixture of Toluene: 1-Methyl-4-(1-methylethenil)-cyclohexene (limonene) and the fourth column is heated to a temperature from 40 to 70° C. and energy is applied by ultrasound or radiation by microwaves.

9. A process of extraction, quantification and recovery of additives in polypropylene comprising the following stages:
    stage 1) washing a plastic material (A);
    stage 2) grinding the plastic material (A) to a particle size from 10 to 500 microns;
    stage 3) carrying out an extraction process where the plastic material (A) of stage 2) is transferred to a first column and thereafter the plastic material (A) passes through a second column, a third column and a fourth column respectively for successive extractions with a first solvent, a second solvent, a third solvent and a fourth solvent, respectively, to obtain a first, second, third and fourth solvent with additives;

stage 4) carrying out packed column extraction, wherein the first, second, third and fourth solvent with the additives obtained from each extraction in the first, second, third and fourth columns from stage 3) passes through a first packed column a second packed column, a third packed column and a fourth packed column respectively to obtain a first additive, a second additive, a third additive and fourth additive;

stage 5) crystallizing the additives obtained from each extraction stage in the first, second, third and fourth packed columns respectively from stage 4); and stage 6) quantifying the crystallized additives obtained from stage 5);

wherein a residue material without additives is subjected to a subsequent pyrolysis process, and wherein in stage 3), a solid-liquid extraction is performed in the first column from 2 to 3 hours with the first solvent, wherein the first solvent is 1-Methyl-4-(1-methylethenil)-cyclohexene (limonene) and the first column is heated to a temperature from 40 to 70° C. and energy is applied by ultrasound or radiation by microwaves.

10. A process of extraction, quantification and recovery of additives in polypropylene comprising the following stages:

stage 1) washing a plastic material (A);

stage 2) grinding the plastic material (A) to a particle size from 10 to 500 microns;

stage 3) carrying out an extraction process where the plastic material (A) of stage 2) is transferred to a first column and thereafter the plastic material (A) passes through a second column, a third column and a fourth column respectively for successive extractions with a first solvent, a second solvent, a third solvent and a fourth solvent, respectively, to obtain a first, second, third and fourth solvent with additives;

stage 4) carrying out packed column extraction, wherein the first, second, third and fourth solvent with the additives obtained from each extraction in the first, second, third and fourth columns from stage 3) passes through a first packed column a second packed column, a third packed column and a fourth packed column respectively to obtain a first additive, a second additive, a third additive and fourth additive;

stage 5) crystallizing the additives obtained from each extraction stage in the first, second, third and fourth packed columns respectively from stage 4); and stage 6) quantifying the crystallized additives obtained from stage 5);

wherein a residue material without additives is subjected to a subsequent pyrolysis process, and wherein the second column contains the second solvent, wherein the second solvent is a mixture of cyclohexane: 1-Methyl-4-(1-methylethenil)-cyclohexene (limonene) in ratios ranging from 20:80 to 80:20 and the second column is heated to a temperature from 40 to 70° C. and energy is applied by ultrasound or radiation by microwaves.

11. A process of extraction, quantification and recovery of additives in polypropylene comprising the following stages:

stage 1) washing a plastic material (A);

stage 2) grinding the plastic material (A) to a particle size from 10 to 500 microns;

stage 3) carrying out an extraction process where the plastic material (A) of stage 2) is transferred to a first column and thereafter the plastic material (A) passes through a second column, a third column and a fourth column respectively for successive extractions with a first solvent, a second solvent, a third solvent and a fourth solvent, respectively, to obtain a first, second, third and fourth solvent with additives;

stage 4) carrying out packed column extraction, wherein the first, second, third and fourth solvent with the additives obtained from each extraction in the first, second, third and fourth columns from stage 3) passes through a first packed column a second packed column, a third packed column and a fourth packed column respectively to obtain a first additive, a second additive, a third additive and fourth additive;

stage 5) crystallizing the additives obtained from each extraction stage in the first, second, third and fourth packed columns respectively from stage 4); and stage 6) quantifying the crystallized additives obtained from stage 5);

wherein a residue material without additives is subjected to a subsequent pyrolysis process, and wherein in stage 3), the third column contains the third solvent, wherein the third solvent is a mixture of toluene: cyclohexane in ratios ranging from 20:80 to 80:20 and the third column is heated to a temperature from 40 to 70° C. and energy is applied by ultrasound or radiation by microwaves.

12. A process of extraction, quantification and recovery of additives in polypropylene comprising the following stages:

stage 1) washing a plastic material (A);

stage 2) grinding the plastic material (A) to a particle size from 10 to 500 microns;

stage 3) carrying out an extraction process where the plastic material (A) of stage 2) is transferred to a first column and thereafter the plastic material (A) passes through a second column, a third column and a fourth column respectively for successive extractions with a first solvent, a second solvent, a third solvent and a fourth solvent, respectively, to obtain a first, second, third and fourth solvent with additives;

stage 4) carrying out packed column extraction, wherein the first, second, third and fourth solvent with the additives obtained from each extraction in the first, second, third and fourth columns from stage 3) passes through a first packed column a second packed column, a third packed column and a fourth packed column respectively to obtain a first additive, a second additive, a third additive and fourth additive;

stage 5) crystallizing the additives obtained from each extraction stage in the first, second, third and fourth packed columns respectively from stage 4); and stage 6) quantifying the crystallized additives obtained from stage 5);

wherein a residue material without additives is subjected to a subsequent pyrolysis process, and wherein in stage 3), a solid-liquid extraction is performed in the fourth column from 2 to 3 hours with the fourth solvent, wherein the fourth solvent is a mixture of Toluene: 1-Methyl-4-(1-methylethenil)-cyclohexene (limonene) and the fourth column is heated to a temperature from 40 to 70° C. and energy is applied by ultrasound or radiation by microwaves.

* * * * *